(12) United States Patent
Johnson

(10) Patent No.: US 9,127,338 B2
(45) Date of Patent: *Sep. 8, 2015

(54) HYPERELASTIC SHAPE SETTING DEVICES AND FABRICATION METHODS

(71) Applicant: Ormco Corporation, Orange, CA (US)

(72) Inventor: Alfred David Johnson, San Leandro, CA (US)

(73) Assignee: Ormco Corporation, Orange, CA (US)

( * ) Notice: Subject to any disclaimer, the term of this patent is extended or adjusted under 35 U.S.C. 154(b) by 307 days.

This patent is subject to a terminal disclaimer.

(21) Appl. No.: 13/777,216

(22) Filed: Feb. 26, 2013

(65) Prior Publication Data

US 2013/0177862 A1 Jul. 11, 2013

Related U.S. Application Data

(60) Division of application No. 12/952,002, filed on Nov. 22, 2010, now Pat. No. 8,382,917, which is a continuation-in-part of application No. 11/949,663, filed on Dec. 3, 2007, now Pat. No. 7,842,143.

(51) Int. Cl.
| | |
|---|---|
| *A61C 7/20* | (2006.01) |
| *C22C 9/01* | (2006.01) |
| *C22F 1/00* | (2006.01) |
| *C30B 29/52* | (2006.01) |
| *C30B 33/02* | (2006.01) |

(52) U.S. Cl.
CPC ... *C22F 1/00* (2013.01); *A61C 7/20* (2013.01); *C22C 9/01* (2013.01); *C22F 1/006* (2013.01); *C30B 29/52* (2013.01); *C30B 33/02* (2013.01)

(58) Field of Classification Search
None
See application file for complete search history.

(56) References Cited

U.S. PATENT DOCUMENTS

| | | |
|---|---|---|
| 368,425 A | 8/1887 | Ross et al. |
| 538,593 A | 4/1895 | Naylor, Jr. |
| 1,560,335 A | 11/1925 | Czochralski |
| 1,904,828 A | 4/1933 | Green |
| 1,913,035 A | 6/1933 | Loepsinger |
| 1,926,925 A | 9/1933 | Wescott |
| 2,060,593 A | 11/1936 | Schaurte et al. |
| 2,371,614 A | 3/1945 | Graves |
| 2,586,556 A | 2/1952 | Mullikin |

(Continued)

FOREIGN PATENT DOCUMENTS

| | | |
|---|---|---|
| EP | 0053596 A1 | 6/1982 |
| EP | 0310439 A1 | 4/1989 |

(Continued)

OTHER PUBLICATIONS

Antonov et al.; New Advances and Developments in the Stepanov Method for the Growth of Shaped Crystals; Crystallography Reports; vol. 47; Suppl. 1; 2002; pp. S43-S52.

(Continued)

*Primary Examiner* — George Wyszomierski
(74) *Attorney, Agent, or Firm* — Wood, Herron & Evans, LLP

(57) ABSTRACT

Dental arches of single-crystal shape memory alloys, methods of fabrication and apparatus for fabrication. The methods include drawing a single crystal of a shape memory alloy from a melt of the alloy. This is followed by heating, forming, and quenching the crystal sufficiently rapid to limit the formation of alloy precipitates to an amount which retains hyperelastic composition and properties of the crystal.

9 Claims, 4 Drawing Sheets

(56) References Cited

U.S. PATENT DOCUMENTS

| | | |
|---|---|---|
| 2,608,996 A | 9/1952 | Forman |
| 2,610,300 A | 9/1952 | Walton et al. |
| 2,647,017 A | 7/1953 | Coulliette |
| 2,911,504 A | 11/1959 | Cohn |
| 3,229,956 A | 1/1966 | White |
| 3,351,463 A | 11/1967 | Rozner et al. |
| 3,357,432 A | 12/1967 | Sparks |
| 3,400,906 A | 9/1968 | Stocklin |
| 3,408,890 A | 11/1968 | Bochman, Jr. |
| 3,435,823 A | 4/1969 | Edwards |
| 3,445,086 A | 5/1969 | Quinn |
| 3,454,286 A | 7/1969 | Anderson et al. |
| 3,546,996 A | 12/1970 | Grijalva et al. |
| 3,559,641 A | 2/1971 | Lay |
| 3,561,537 A | 2/1971 | Dix et al. |
| 3,613,732 A | 10/1971 | Willson et al. |
| 3,620,212 A | 11/1971 | Fannon, Jr. et al. |
| 3,659,625 A | 5/1972 | Coiner et al. |
| 3,725,835 A | 4/1973 | Hopkins et al. |
| 3,789,838 A | 2/1974 | Fournier et al. |
| 3,849,756 A | 11/1974 | Hickling |
| 3,888,975 A | 6/1975 | Ramwell |
| 3,913,572 A | 10/1975 | Wheeler |
| 3,918,443 A | 11/1975 | Vennard et al. |
| 3,974,844 A | 8/1976 | Pimentel |
| 4,055,955 A | 11/1977 | Johnson |
| 4,063,831 A | 12/1977 | Meuret |
| 4,072,159 A | 2/1978 | Kurosawa |
| 4,096,993 A | 6/1978 | Behr |
| 4,151,064 A | 4/1979 | Kuehnle |
| 4,176,719 A | 12/1979 | Bray |
| 4,177,327 A | 12/1979 | Mathews et al. |
| 4,195,773 A | 4/1980 | Ogden |
| 4,243,963 A | 1/1981 | Jameel et al. |
| 4,265,684 A | 5/1981 | Boll |
| 4,279,790 A | 7/1981 | Nakajima |
| 4,340,049 A | 7/1982 | Munsch |
| 4,485,545 A | 12/1984 | Caverly |
| 4,501,058 A | 2/1985 | Schutzler |
| 4,524,343 A | 6/1985 | Morgan et al. |
| 4,549,717 A | 10/1985 | Dewaegheneire |
| 4,551,974 A | 11/1985 | Yaeger et al. |
| 4,553,393 A | 11/1985 | Ruoff |
| 4,558,715 A | 12/1985 | Walton et al. |
| 4,567,549 A | 1/1986 | Lemme |
| 4,585,209 A | 4/1986 | Aine et al. |
| 4,589,179 A | 5/1986 | Hulting, Jr. |
| 4,596,483 A | 6/1986 | Gabriel |
| 4,619,284 A | 10/1986 | Delarue et al. |
| 4,654,191 A | 3/1987 | Krieg |
| 4,684,913 A | 8/1987 | Yaeger |
| 4,706,758 A | 11/1987 | Johnson |
| 4,753,465 A | 6/1988 | Dalby |
| 4,821,997 A | 4/1989 | Zdeblick |
| 4,823,607 A | 4/1989 | Howe et al. |
| 4,824,073 A | 4/1989 | Zdeblick |
| 4,848,388 A | 7/1989 | Waldbusser |
| 4,854,797 A | 8/1989 | Gourd |
| 4,864,824 A | 9/1989 | Gabriel et al. |
| 4,893,655 A | 1/1990 | Anderson |
| 4,896,728 A | 1/1990 | Wolff et al. |
| 4,943,032 A | 7/1990 | Zdeblick |
| 5,060,888 A | 10/1991 | Vezain et al. |
| 5,061,137 A | 10/1991 | Gourd |
| 5,061,914 A | 10/1991 | Busch et al. |
| 5,069,419 A | 12/1991 | Jerman |
| 5,072,288 A | 12/1991 | MacDonald et al. |
| 5,102,276 A | 4/1992 | Gourd |
| 5,114,504 A | 5/1992 | AbuJudom, II et al. |
| 5,116,252 A | 5/1992 | Hartman |
| 5,117,916 A | 6/1992 | Ohta et al. |
| 5,119,555 A | 6/1992 | Johnson |
| 5,129,753 A | 7/1992 | Wesley et al. |
| 5,160,233 A | 11/1992 | McKinnis |
| 5,190,546 A | 3/1993 | Jervis |
| 5,192,147 A | 3/1993 | McCloskey |
| 5,211,371 A | 5/1993 | Coffee |
| 5,218,998 A | 6/1993 | Bakken et al. |
| 5,245,738 A | 9/1993 | Johnson |
| 5,309,717 A | 5/1994 | Minch |
| 5,312,152 A | 5/1994 | Woebkenberg, Jr. et al. |
| 5,325,880 A | 7/1994 | Johnson et al. |
| 5,344,117 A | 9/1994 | Trah et al. |
| 5,364,046 A | 11/1994 | Dobbs et al. |
| 5,494,113 A | 2/1996 | Polan |
| 5,502,982 A | 4/1996 | Venetucci |
| 5,543,349 A | 8/1996 | Kurtz et al. |
| 5,605,543 A | 2/1997 | Swanson |
| 5,619,177 A | 4/1997 | Johnson et al. |
| 5,622,225 A | 4/1997 | Sundholm |
| 5,640,217 A | 6/1997 | Hautcoeur et al. |
| 5,641,364 A | 6/1997 | Golberg et al. |
| 5,676,356 A | 10/1997 | Ekonen et al. |
| 5,695,504 A | 12/1997 | Gifford, III et al. |
| 5,714,690 A | 2/1998 | Burns et al. |
| 5,722,989 A | 3/1998 | Fitch et al. |
| 5,771,742 A | 6/1998 | Bokaie et al. |
| 5,772,378 A | 6/1998 | Keto-Tokoi |
| 5,796,152 A | 8/1998 | Carr et al. |
| 5,819,749 A | 10/1998 | Lee et al. |
| 5,825,275 A | 10/1998 | Wuttig et al. |
| 5,837,394 A | 11/1998 | Schumm, Jr. |
| 5,840,199 A | 11/1998 | Warren |
| 5,850,837 A | 12/1998 | Shiroyama et al. |
| 5,867,302 A | 2/1999 | Fleming |
| 5,903,099 A | 5/1999 | Johnson et al. |
| 5,916,178 A | 6/1999 | Noone et al. |
| 5,924,492 A | 7/1999 | Kikuchi et al. |
| 5,930,651 A | 7/1999 | Terasawa |
| 5,960,812 A | 10/1999 | Johnson |
| 6,042,553 A | 3/2000 | Solar et al. |
| 6,072,617 A | 6/2000 | Henck |
| 6,073,700 A | 6/2000 | Tsuji et al. |
| 6,075,239 A | 6/2000 | Aksyuk et al. |
| 6,080,160 A | 6/2000 | Chen et al. |
| 6,084,849 A | 7/2000 | Durig et al. |
| 6,101,164 A | 8/2000 | Kado et al. |
| 6,110,204 A | 8/2000 | Lazarov et al. |
| 6,124,523 A | 9/2000 | Banas et al. |
| 6,126,371 A | 10/2000 | McCloskey |
| 6,139,143 A | 10/2000 | Brune et al. |
| 6,195,478 B1 | 2/2001 | Fouquet |
| 6,203,715 B1 | 3/2001 | Kim et al. |
| 6,229,640 B1 | 5/2001 | Zhang |
| 6,247,493 B1 | 6/2001 | Henderson |
| 6,277,133 B1 | 8/2001 | Kanesaka |
| 6,284,067 B1 | 9/2001 | Schwartz et al. |
| 6,358,380 B1 | 3/2002 | Mann et al. |
| 6,386,507 B2 | 5/2002 | Dhuler et al. |
| 6,406,605 B1 | 6/2002 | Moles |
| 6,407,478 B1 | 6/2002 | Wood et al. |
| 6,410,360 B1 | 6/2002 | Steenberge |
| 6,447,478 B1 | 9/2002 | Maynard |
| 6,451,668 B1 | 9/2002 | Neumeier et al. |
| 6,454,913 B1 | 9/2002 | Rasmussen et al. |
| 6,470,108 B1 | 10/2002 | Johnson |
| 6,475,261 B1 | 11/2002 | Matsumoto et al. |
| 6,524,322 B1 | 2/2003 | Berreklouw |
| 6,533,905 B2 | 3/2003 | Johnson et al. |
| 6,537,310 B1 | 3/2003 | Palmaz et al. |
| 6,582,985 B2 | 6/2003 | Cabuz et al. |
| 6,592,724 B1 | 7/2003 | Rasmussen et al. |
| 6,596,102 B2 | 7/2003 | Homma |
| 6,605,111 B2 | 8/2003 | Bose et al. |
| 6,614,570 B2 | 9/2003 | Johnson et al. |
| 6,620,634 B2 | 9/2003 | Johnson et al. |
| 6,624,730 B2 | 9/2003 | Johnson et al. |
| 6,669,794 B1 | 12/2003 | Bellouard et al. |
| 6,669,795 B2 | 12/2003 | Johnson et al. |
| 6,672,502 B1 | 1/2004 | Paul et al. |
| 6,688,828 B1 | 2/2004 | Post |
| 6,729,599 B2 | 5/2004 | Johnson |
| 6,742,761 B2 | 6/2004 | Johnson et al. |
| 6,746,890 B2 | 6/2004 | Gupta et al. |

(56) References Cited

U.S. PATENT DOCUMENTS

| | | | |
|---|---|---|---|
| 6,771,445 | B1 | 8/2004 | Hamann et al. |
| 6,790,298 | B2 | 9/2004 | Johnson et al. |
| 6,811,910 | B2 | 11/2004 | Tsai et al. |
| 6,840,329 | B2 | 1/2005 | Kikuchi et al. |
| 6,843,465 | B1 | 1/2005 | Scott |
| 6,908,275 | B2 | 6/2005 | Nelson et al. |
| 6,920,966 | B2 | 7/2005 | Buchele et al. |
| 6,955,187 | B1 | 10/2005 | Johnson |
| 7,040,323 | B1 | 5/2006 | Menchaca et al. |
| 7,044,596 | B2 | 5/2006 | Park |
| 7,073,504 | B2 | 7/2006 | Callister et al. |
| 7,084,726 | B2 | 8/2006 | Gupta et al. |
| 7,201,367 | B2 | 4/2007 | Wietharn |
| 7,422,403 | B1 | 9/2008 | Johnson et al. |
| 7,441,888 | B1 | 10/2008 | Johnson |
| 7,540,899 | B1 | 6/2009 | Johnson |
| 7,544,257 | B2 * | 6/2009 | Johnson et al. ............... 148/562 |
| 7,586,828 | B1 | 9/2009 | Ma |
| 7,632,361 | B2 | 12/2009 | Johnson et al. |
| 7,736,687 | B2 | 6/2010 | Sims et al. |
| 7,763,342 | B2 | 7/2010 | Johnson |
| 7,793,911 | B2 | 9/2010 | Fontana et al. |
| 7,842,143 | B2 | 11/2010 | Johnson et al. |
| 8,007,674 | B2 | 8/2011 | Johnson |
| 8,382,917 | B2 | 2/2013 | Johnson |
| 8,556,969 | B2 * | 10/2013 | Johnson ..................... 623/11.11 |
| 2001/0023010 | A1 | 9/2001 | Yamada et al. |
| 2002/0018325 | A1 | 2/2002 | Nakatani et al. |
| 2002/0062154 | A1 | 5/2002 | Ayers |
| 2002/0106614 | A1 | 8/2002 | Prince et al. |
| 2003/0002994 | A1 | 1/2003 | Johnson et al. |
| 2003/0078465 | A1 | 4/2003 | Pai et al. |
| 2003/0170130 | A1 | 9/2003 | Johnson |
| 2004/0083006 | A1 | 4/2004 | Ellingsen et al. |
| 2004/0200551 | A1 | 10/2004 | Brhel et al. |
| 2004/0221614 | A1 | 11/2004 | Holemans et al. |
| 2004/0243219 | A1 | 12/2004 | Fischer et al. |
| 2004/0249399 | A1 | 12/2004 | Cinquin et al. |
| 2005/0113933 | A1 | 5/2005 | Carter et al. |
| 2006/0118210 | A1 | 6/2006 | Johnson |
| 2006/0213522 | A1 | 9/2006 | Menchaca et al. |
| 2006/0232374 | A1 | 10/2006 | Johnson |
| 2007/0137740 | A1 | 6/2007 | Johnson et al. |
| 2007/0207321 | A1 | 9/2007 | Abe et al. |
| 2007/0210201 | A1 | 9/2007 | Palumbo et al. |
| 2007/0246233 | A1 | 10/2007 | Johnson |
| 2009/0095493 | A1 | 4/2009 | Johnson et al. |
| 2009/0183986 | A1 | 7/2009 | Johnson et al. |
| 2009/0187243 | A1 | 7/2009 | Johnson |
| 2010/0006304 | A1 | 1/2010 | Johnson et al. |

FOREIGN PATENT DOCUMENTS

| | | |
|---|---|---|
| EP | 1122526 A2 | 8/2001 |
| EP | 1238600 A1 | 9/2002 |
| GB | 2187951 A | 9/1987 |
| JP | 57161031 A | 10/1982 |
| JP | 59179771 A | 10/1984 |
| JP | 07090624 B | 10/1995 |
| JP | 10173306 A | 6/1998 |
| JP | 2000185999 A | 7/2000 |
| SU | 1434314 A1 | 10/1988 |
| WO | 98/53362 A2 | 11/1998 |
| WO | 99/16387 A1 | 4/1999 |
| WO | 99/62432 A1 | 12/1999 |
| WO | 0004204 A1 | 1/2000 |
| WO | 03/052150 A2 | 6/2003 |
| WO | 2005/108635 A2 | 11/2005 |
| WO | 2006/019943 A1 | 2/2006 |

OTHER PUBLICATIONS

ElastaMet™ Hyperelastic Single Cyrstal Metal Alloys, Brochure from New Discovery Metals; 2007, 1 pg.

ElastaMet™ The Metal, website screen capture, accessed Jul. 23, 2008, 3 pp.

Fu et al.; The Growth Characteristics with a Shape Memory Effect; J. Phys.: Condens. Matter; vol. 4; 1992; pp. 8303-8310.

Morgan, N.B.; Medical Shape Memory Alloy Applications—the Market and its Products; Materials Science and Engineering A 378; 2004; pp. 16-23.

Qingfu et al.; Stabilisation of Martensite During Training of Cu—Al—Ni Single Crystals; Journal de Physique IV; Colloque C2; Supplement to the Journal de Physique III; vol. 5; Feb. 1995; pp. 181-186.

Recarte et al.; Influence of Al and Ni Concentration on the Martensitic Transformation in Cu—Al—Ni Shape-Memory Alloys; Metallurgical and Materials Transactions A; vol. 33A; Aug. 2002; pp. 2581-2591.

Sittner et al.; Stress Induced Martensitic Transformations in Tension/ Torsion of CuAlNi Single Crystal Tube; Scripta Materialia; vol. 48; 2003; pp. 1153-1159.

Sutuo et al.; Development of Medical Guide Wire of Cu—Al—Mn- Base Superelastic Alloy with Functionally Graded Characteristics; Mater Res Part B: Appl Biomater; vol. 69B; 2004; pp. 64-69.

Zhang et al.; The Variant Selection Criteria in Single-Crystal CuAlNi Shape Memory Alloys; Smart Mater. Struct.; vol. 9; 2000; pp. 571- 581.

Zhdanov et al.; Thermal Stresses in Tubes, Produced from a Melt by the Stepanov Method, During their Cooling; Journal of Engineering Physics and Thermophysics; vol. 68; No. 1; 1995; pp. 80-89.

Dario et al.; Shape Memory Alloy Microactuators for Minimal Invasive Surgery; Proceedings of SMST-94 Conference; pp. 427- 433; Pacific Grove CA; 1994.

Johnson, A. D.; Vacuum-Deposited TiNi Shape Memory Film: Characterization and Applications in Microdevices; J. Micromech. Microeng.; vol. 1; pp. 34-41; 1991.

Krulevitch et al.; Thin Film Shape Memory Alloy Microactuators; J. Micromech. Microeng.; vol. 5; No. 4; 26 pgs.; 1996.

Schetky, L.M.; Shape-Memory Alloys; Scientific American, pp. 74-82; 1979.

Viahhi et al.; Robototechnic Constructions Based on Cu—Al—Ni Single Crystal Actuators; Proceedings of Second International Conference on Shape Memory and Superelastic Technologies; 1997; United States.

Pauling, Linus, College Chemistry, Second Edition, W.H. Freeman and Company, San Francisco, 1955, pp. 81-91.

Buchaillot L. et al., Thin Film of Titanium/Nickel Shape Memory Alloy for Multi-Degree of Freedom Microactuators, Seisan Kenkyu, vol. 51, No. 8, 1999, pp. 22-23.

Johnson A. D. et al., Applications of Shape Memory Alloys: Advantages, Disadvantages, and Limitations, Micromachining and Microfabrication Process Technology VII, Oct. 22-24, 2001, San Francisco, CA, USA, vol. 4557, 2001, pp. 341-351.

Takabayashi et al., Reversible Shape Memory Alloy Film Fabricated by RF Sputtering, Materials and Manufacturing Processes, vol. 13, No. 2, 1998, pp. 275-286.

Martynov, V., TiNi Thin Films for Microactuators and Microdevices: Sputter Deposition and Processing Techniques, Thermec' 2003, Internat'l Conf. on Processing and Manufacturing of Advanced Materials, Jul. 7-11, 2003, Leganes, Madrid, Spain, Materials Science Forum, Jul. 7, 2003 vol. 426-432; pp. 3475-3480.

dos Santos et al.; The Application of Shape Memory Actuators in Anthropomorphic Upper Limb Prostheses; Artif. Organs; vol. 27; No. 5; pp. 473-477; 2003.

Gill et al.; Three-Dimensional Thin-Film Shape Memory Alloy Microactuator With Two-Way Effect; Journal of Microelectromechanical Sys.; vol. 11; No. 1; Feb. 2002; pp. 68-77.

Pauling, Linus, College Chemistry, Second Edition, W.H. Freeman and Company, San Francisco, 1955, pp. 81-81.

http://ww.algor.com/news_pub/tech_reports/2005/rubber & Foam/default.asp.-

(56) References Cited

OTHER PUBLICATIONS

Wang et al., Temperature Memory Effect in CuAlNi Single Crystalline and CuZnAl Polycrystalline Shape Memory Alloys; Thermochimica Acta, vol. 448, 2006, pp. 69-72.

Yahia et al., Bioperformance of Shape Memory Alloy Single Crystals; Bio-Medical Materials and Engineering, vol. 16, 2006, pp. 101-118.

Zhang et al., Nanoscale Pseudoelasticity of Single-Crystal Cu—Al—Ni Shape-Memory Alloy Induced by Cyclic Nanoindentation, J. Mater Sci, vol. 41, 2006, pp. 5021-5024.

Creuziger et al., Initial Transformation Around a Notch Tip in CuAlNi: Experiment and Modeling; Acta Materialia, vol. 56, pp. 518-526, 2008.

* cited by examiner

HYPERELASTIC SHAPE SETTING DEVICES AND FABRICATION METHODS

CROSS REFERENCE TO RELATED APPLICATIONS

This application is a divisional of U.S. Pat. No. 8,382,917 entitled HYPERELASTIC SHAPE SETTING DEVICES AND FABRICATION METHODS, which claims priority to U.S. Pat. No. 7,842,143 also entitled HYPERELASTIC SHAPE SETTING DEVICES AND FABRICATION METHODS, the disclosures of which are incorporated herein by reference in their entirety as if completely set forth herein below.

STATEMENT AS TO FEDERALLY SPONSORED RESEARCH

This invention was made with Government support under Contract No. W31P4Q-05-C-0158 awarded by DARPA. The Government has certain rights in the invention.

FIELD OF THE INVENTION

This invention relates to mechanical devices that have a component in which large recoverable distortions are available in elongated shapes.

BACKGROUND OF THE INVENTION

Common shape memory alloy (also called SMA) materials such as Nitinol can be shape-set by heating to an annealing temperature while constrained to a shape, and then cooling. For example, a helix may be formed from a straight TiNi wire by winding the wire on a mandrel, securing the ends, heating to 550° C., and cooling. The rates of heating and cooling are not critical in this "shape-setting" process for TiNi, although special characteristics are achieved by holding the temperature constant at specific temperatures.

It is a general object of the invention to provide methods for the shape setting fabrication of single crystal shape memory alloys (also called "hyperelastic"), such as CuAlNi, CuAlMn, CuAlBe, CuAlNb and others, and to provide devices made by such methods.

A further object of this invention is to provide new and improved devices made of hyperelastic single crystal SMA by novel methods of shape-setting.

In particular, it is the object of the invention to provide new and improved SMA wires which may be used for orthodontic archwires.

In orthodontics, a standard procedure to correct malocclusions is to attach individual teeth to a flexible component called an archwire. These archwires are generally of a simple curved shape as illustrated in the FIG. 3. Examples of stainless steel and titanium-nickel dental arches are described and illustrated on the website ORMCO.com. Dental arches are commonly made of wire of round or rectangular cross-section. Round wires range in wire diameter from 0.013 to 0.026 inches, while rectangular cross-section arches may be as small as 0.016 by 0.016 inches or a large as 0.020 by 0.030 inches.

Millions of orthodontic archwires are sold in the U.S. each year. Titanium-nickel-based alloys have taken market share because they have elasticity superior to that of stainless steel. Increased elasticity enables the orthodontist to move teeth to their desired position with fewer adjustments and fewer replacements of the archwire.

A useful application of hyperelastic wire is in dental arches. For example, archwires made of hyperelastic alloy may have four important advantages over TiNi-based wires: (1) recoverable strain is increased from 3-5% to 9-12%; (2) force exerted by a hyperelastic wire is less than the force exerted by a TiNi wire of comparable thickness; (3) the force is constant over a displacement of 9% strain; and (4) the return force is nearly equal to the displacing force because the mechanical hysteresis is very small. Because of these advantages, hyperelastic archwires may potentially replace titanium-nickel-based archwires in a large percentage of orthodontic procedures. At least one archwire manufacturer has been seeking a new material with these advantages. Unfortunately, typical methods of fabricating such wires may not work for the fabrication of hyperelastic materials.

For convenience of use, straight wires are typically formed into an arch shape that approximately conforms to the shape of the jaw of the patient, a process known as shape-setting. TiNi based alloy wires are shape-set by winding on a mandrel having the desired arch shape, annealing by heating in a furnace to 500° C. or higher, and allowing the shaped wires to cool. This shape-setting process may take an hour or more.

The process described for shape-setting TiNi based wire cannot be used for shape-setting hyperelastic wire. Hyperelastic wire, typically single crystal, is not thermodynamically stable. At elevated temperatures of several hundred degrees, one or more of the components (especially Al) gradually forms precipitates. These precipitates remove the element from the crystal lattice, effectively changing the composition and hence the transition temperature of the alloy. A wire heated to 500° C. and cooled over a period of several minutes has no shape memory and no superelasticity.

This property, the precipitation of Al at high temperature, can be avoided if the wire is heated and cooled rapidly, for example in a few seconds. It is impractical to quickly heat and cool a mandrel of mass sufficient to impart the desired shape. This has led us to the invention of a novel process for shape-setting hyperelastic wires for orthodontic arches, as described herein.

The present invention accomplishes, using a novel method, the purpose of imparting an arch shape to a straight hyperelastic wire while preserving its elasticity and transition temperature.

SUMMARY OF THE INVENTION

The present invention relates to methods for shape setting hyperelastic materials, such as single-crystal Cu-based shape memory alloys (SMAs). In particular, the methods described herein include methods of forming hyperelastic materials into dental appliances, including dental archwires.

For example, described herein are methods of shape-setting a wire of single-crystal shape memory alloy into an arched wire shape while maintaining its integrity as a single crystal shape memory alloy. The method may include the steps of: heating the wire to a first temperature sufficient for annealing the alloy; forcing the wire into an arched shape while the wire is held at the first temperature, wherein the heating and forcing steps are performed in less than 10 seconds; and rapidly cooling the alloy to room temperature sufficiently quickly to cause the alloy to form a single-crystal. In some variations, these methods may also include the steps of pulling the single crystal wire.

The step of heating the wire may be performed for less than 1 second or for up to about 10 seconds. The step of rapid cooling is performed for less than about 0.5 second. For example, the steps of heating, forcing and cooling may all be performed in less than about 5 seconds, less than about 2 seconds, or less than about 1 second.

In some variations, the step of forcing the wire into an arched shape comprises rapidly contacting the heated wire with a mandrel. The mandrel may be a copper or stainless steel mandrel, as mentioned. The step of forcing the wire into an arched shape may include dropping the mandrel against the heated wire. For example, the step of forcing the wire into an arched shape may include bringing the mandrel rapidly into contact with the heated wire and allowing the mandrel (now with the wire) to drop into a quenching bath. Thus, the step of rapidly cooling the wire may comprise dropping the heated wire and mandrel into a cooling bath.

The step of forcing the wire into an arched shape may comprise forcing the wire into a dental arch shape having a round diameter of between about 0.013 to about 0.026 inches. In some variations, the step of forcing the wire into an arched shape comprises forcing the wire into a dental arch shape having rectangular dimensions of between about 0.016 by 0.016 inches and about 0.020 by 0.030 inches.

Also described herein are methods of shape-setting a wire of single-crystal alloy into a dental arch so that it is comprised of a single-crystal shape memory alloy. The method may include the steps of: heating the wire to an annealing temperature sufficient for annealing the alloy; forcing the heated wire into a dental arch shape by forcing the wire against a mandrel, wherein the steps of heating and forcing the wire against the mandrel are performed in less than 10 seconds; and rapidly cooling the wire by quenching to a cooling temperature sufficiently quickly to cause the alloy to remain a single-crystal in the dental arch shape.

Also described herein are methods of shape-setting an alloy into a dental arch so that it is comprised of a single-crystal CuAlNi shape memory alloy, the method comprising the steps of: heating a wire of CuAlNi alloy to a first temperature sufficient to place the Cu, Al and Ni in solution; rapidly quenching the alloy to a second temperature to prevent precipitation of the Cu, Al and Ni so that the alloy remains as a single-crystal of CuAlNi; constraining the alloy into a dental arch shape; heating the alloy to a third temperature for a first time period, wherein the third temperature and first time period are sufficient to cause the alloy to lose its strength; and cooling the alloy to a fourth temperature for a second time period, wherein the fourth temperature and second time period are sufficient to cause the alloy to remain a single-crystal in the shape.

Dental arches formed by any of the methods discussed herein are also described. Thus, described herein are dental arches comprising a hyperelastic, single-crystal shape memory material. The dental arch typically has an elongate, curved length that is configured to fit within a human mouth. For example the dental arch may traverse an arc extending approximately 180 degrees in an unstressed state (at rest). In some variations, the dental arch formed of the single crystal shape memory alloy material has a curved elongate length with a round diameter of between about 0.013 to about 0.026 inches. In other variations the dental arch has a curved elongate length with a rectangular cross-section with dimensions of between about 0.016 by 0.016 inches and about 0.020 by 0.030 inches.

As mentioned above, the dental arch may be formed of a single-crystal shape memory alloy of CuAlNi single crystal material. Other single-crystal shape memory alloys may be used, including: CuAlMb single crystal material; CuAlMn single crystal material, CuAlBe single crystal material, and CuAlNb single crystal material. In some variations, four-component alloys may be used. In some variations, special characteristics such as increased ductility may be achieved by substituting all or part of the Ni of CuAlNi with Mn, Fe, Be etc: or by a combination of one or more of these elements. For example, the dental arches described herein may be formed of CuAlNiMn (e.g., single-crystal CuAlNiMb), using the processes and techniques detailed below.

One advantage of the methods for fabricating the single-crystal shape memory alloy dental archwire devices as described herein is that the integrity of the single crystal material forming the final dental archwire is intact when the device is completely formed, and little (if any) post-processing is necessary. The single crystal dental archwires described herein have many advantages, particularly in physical properties, compared to even polycrystalline archwires formed of the same materials (e.g. CuAlNi).

In some variations the dental arch has different regions along the length of the dental arch that have different material properties. For example, the ends of the dental arch wire may be in the martensitic phase at body temperature. During formation of the dental arch wire, the ends may be cooled slowly, so that they are in the martensite phase.

Apparatuses and systems for forming a single-crystal shape memory arch wire are also described herein. In general, these devices and systems are configured to form a wire (including a wire of single-crystal shape memory material) into a dental arch while preserving the single-crystal nature of the wire.

For example, described herein are apparatuses for forming a wire of shape memory alloy into a dental arch while preserving the single-crystal nature of the wire that include: a power source for heating the wire to above an annealing temperature of the shape memory alloy; a holder for holding the ends of the wire so that the wire may be heated by the power source; a mandrel for shaping the wire; a driver for driving the mandrel against the heated wire held by the holder; and a quenching sub-assembly for rapidly quenching the wire connected to the mandrel to room temperature within less than about 1 second.

Any appropriate power source may be used. For example, in some variations the power source is an electrical power supply configured to apply power to the wire to heat the wire to a temperature above the annealing temperature of the shape memory alloy forming the wire. In some variations, the power source is a variable voltage source.

In general, the power source is configured to heat the wire to a temperature around or above the annealing temperature of the shape memory alloy. The power source may hold the wire at this temperature (e.g., greater than 600 degrees in some variations) while waiting for the mandrel to be driven against the wire, before quenching the wire.

The holder may be any holder that is configured to secure the wire within the apparatus so that the wire can be heating above the annealing temperature and then very quickly quenched by the quenching sub-assembly. For example, the holder may include a pair of clamps or graspers. In some variations these graspers are configured to electrically connect the wire to the power source. The clamps or graspers may be configured to secure the wire but allow it to be displaced into the quenching sub-assembly. For example, the clamps may loosely hold the wire or be extendable/releasable to allow the wire to be dropped or driven into the quenching sub-assembly by the mandrel and/or driver (e.g., a plunger).

The mandrel typically comprises an arced shape configured to form a dental arch. For example, the mandrel may be a metal or ceramic material that is shaped into an arch conforming to the dimensions of a dental arch to be formed. The mandrel may include a guide region to bend against the wire and shape it.

In some variations the mandrel is connected to a driver and is configured to drop against the wire (which may be secured by the holder), forming the wire into the shape of the dental arch, and dropping the wire into the quenching sub-assembly. For example, the driver may comprise a plunger.

A quenching sub-assembly is generally configured to cool the wire to an appropriate temperature. For example, the quenching sub-assembly may be a bath configured to hold salt water. The bath may be cooled (e.g., to room temperature or lower).

For example, described herein are apparatuses for forming a wire of shape memory alloy into a dental arch while preserving the single-crystal nature of the wire, the apparatus comprising: a voltage source for heating the wire to above an annealing temperature of the shape memory alloy; a pair of conductive holders for holding the ends of the wire in electrical communication with the voltage source so that the wire can be heated by the power source; a curved mandrel for shaping the wire; a plunger above the mandrel for driving the mandrel against the heated wire held by the holder; and a quenching sub-assembly comprising a bath positioned below the mandrel and plunger and configured to receive the mandrel and wire to rapidly quench the wire to room temperature within less than about 1 second.

DETAILED DESCRIPTION OF THE INVENTION

Hyperelastic alloys formed as single crystals, for example, CuAlNi single crystals of approximately Cu(84)Al(14)Ni(4) wt. %, have enhanced strain recovery properties compared to more conventional polycrystal SMAs such as Nitinol. Such single crystals are formed as extruded shapes whether by pulling from melt or by continuous casting. It is desirable to form other shapes such as helices or bends, but the methodology used for forming Nitinol destroys the single crystallinity; a problem with polycrystal CuAlNi is that it is brittle. Therefore there is a need for methods which avoid these and other problems.

The fabrication and performance of such single crystal SMA materials are disclosed in U.S. application Ser. No. 10/588,412 filed Jul. 31, 2006, the disclosure of which is incorporated by this reference.

Figure 2:
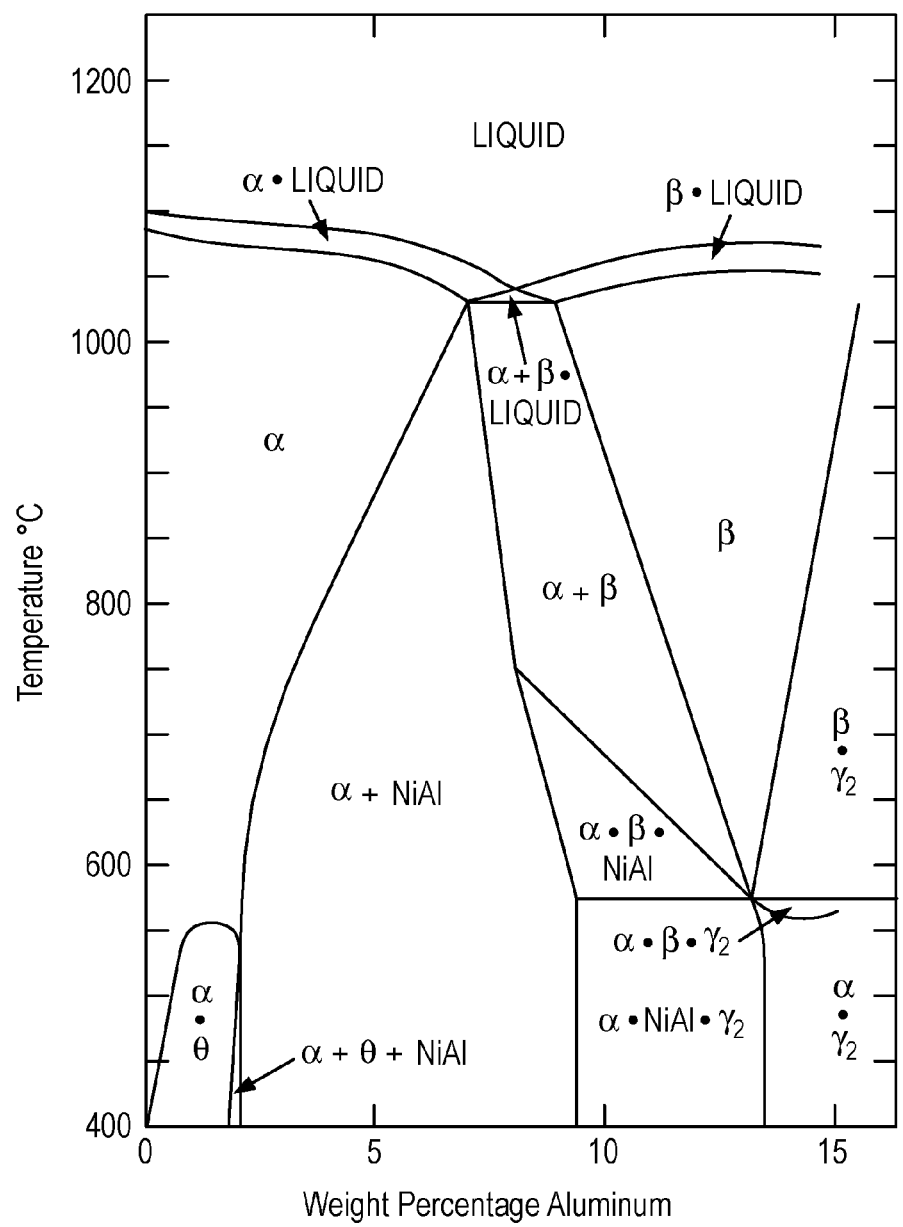
FIG. 2 is a phase diagram of CuAlNi in which the Ni is 3 wt. %.
Figure 3A:
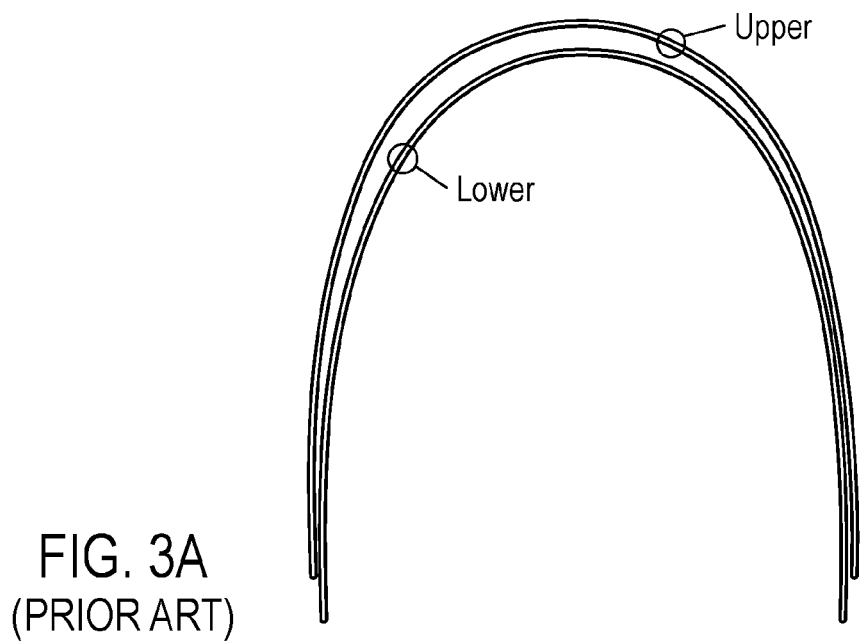
FIG. 3A shows prior art orthodontic archwires for an upper and a lower jaw. It consists of a titanium-nickel wire, 0.016 inches in diameter, formed into an arch. The archwire form is approximately three inches high and three inches wide. The upper and lower archwires may be slightly different shapes. The single crystal archwires described herein may have a similar overall shape, though they may have superior properties resulting from their single crystal nature.
Figure 3B:
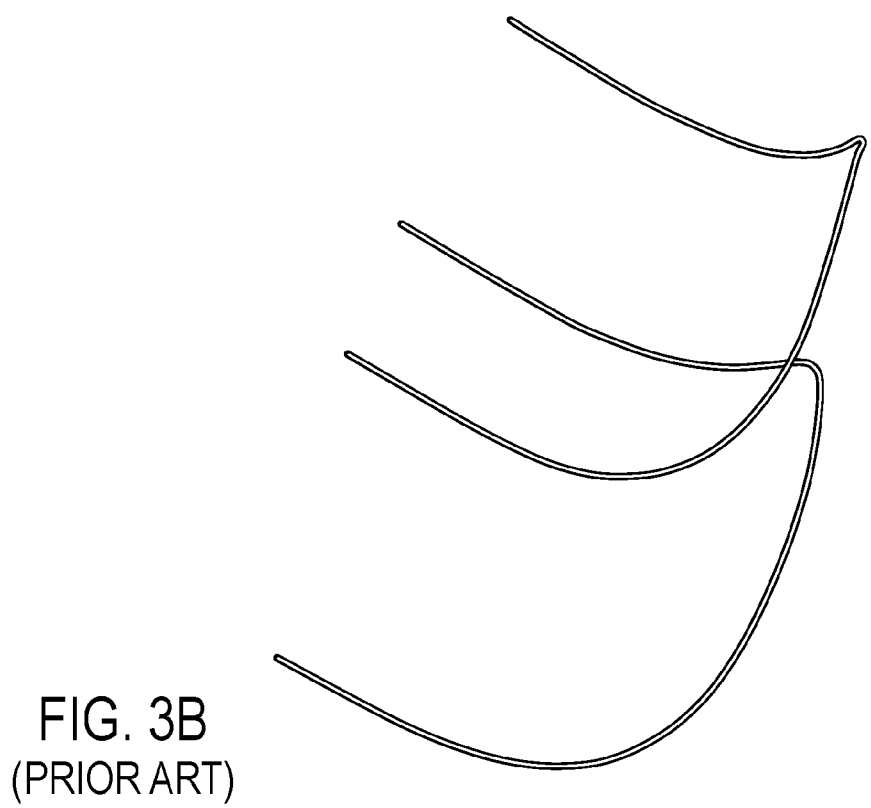
FIG. 3B shows another variation of a prior art dental archwire, referred to as a reverse-curve archwire. Such archwires may include curves in multiple directions.

If single-crystal CuAlNi is drawn from melt and cooled by use of the Stepanov method, as the single crystal cools, precipitates form so that strength, shape memory, and hyperelastic properties are not optimal. Imparting shape memory and hyperelastic properties requires heating to a temperature high enough to dissolve the precipitates, followed immediately by rapid cooling ("quenching") to lock in the dissolved elemental components. Methods used for producing single crystal shape memory alloys generally produce net shapes in the crystal. FIG. 2 shows the phase diagram of CuAlNi in which the Ni is 3 wt. %. Single crystal devices of other shape memory alloys may be formed using the methods described herein, including CuAlMn, CuAlBe, etc.

Use of elevated temperature to modify the shape of hyperelastic single crystal of alloys such as CuAlNi (e.g., CuAlMn, CuAlBe, etc.) normally results in loss of single crystallinity: at elevated temperatures precipitation of elemental components (especially Al) changes the composition. For this reason actuators and flexures designed to exploit the extraordinary strain recovery of these materials (9% strain) have been limited to net shapes (solid and tubular cylinders) produced during formation of the crystal. However, if heating and quenching take place in a very short time (fraction of a second) the precipitation does not progress far enough to cause significant change in the composition and the hyperelastic properties can be retained. These discoveries by the present inventors enable a variety of methods for shape-setting single crystal SMAs. Extruded shapes may be bent, elongated with reduction of diameter, and tubular as well as solid crystal shapes may be re-formed. These novel methods extend the usefulness of single crystal SMA by removing a limitation on shapes.

Single crystals pulled from melt have an as-formed or extruded shape such as a solid or hollow cylindrical shape with a constant cross-sectional form. It is sometimes advantageous to alter the fabricated shape into a shape more suited to a particular application. One such application is for use as eyeglass frame hinge flexures to replace hinges or to replace the entire eyeglass frame. Another is to form curves in a guidewire to follow tortuous paths in a blood vessel, or a sieve placed in a blood vessel for the purpose of retrieving and removing a blood clot. Another form is the dental archwire mentioned above. The various embodiments of the present invention provide processes for "shape-setting" CuAlNi, CuAlMn, CuAlBe, or other single-crystal materials.

For example, CuAlNi single crystal is in a metastable condition and gradually deteriorates to polycrystalline form. The rate of decomposition is temperature dependent. At room temperature the rate is sufficiently low that negligible change takes place over years. At 300-400° C., the rate is rapid enough that degeneration to multiple crystals may occur in a few seconds. Once formed, the multiple crystals do not re-form as a single crystal: this requires melting and special processing. However, CuAlNi may retain its single crystal condition through repeated heating to annealing temperature and rapid cooling. At sufficiently high temperature (typically 850-950° C.) the three components Cu, Al, and Ni are in solution. CuAlNi's hyperelastic properties are exhibited within a very narrow range of compositions. If cooling is not sufficiently rapid, Al precipitates from the solution, changing the composition and drastically altering thermo-mechanical properties.

The crucial insight leading to the present invention is that a combination of annealing, constrained shaping, and quenching leads to an altered "remembered" shape.

Quenching, that is rapidly lowering the temperature from a temperature at which the three components Cu, Al, and Ni are in solution, is conventionally used to "freeze in" the composition by not permitting elemental components from forming precipitates. If cooling takes place slowly these precipitates remove atoms from the crystal lattice and modify it in such a way as to destroy the phase transformation that leads to the shape memory effect. Rapid cooling preserves the integrity of the solution.

Composition can be altered during heating and cooling cycles by the fact that Al at the surface forms aluminum oxide, and the oxide, being insoluble, is effectively removed from the material. Reducing the Al content by 0.1%, which increases the phase transformation temperature, may alter the transition point enough to make the material useless.

It is a common characteristic of metals that there is a temperature range below the melting point within which internal stresses are minimal. Such an "annealed" material can be deformed far beyond its natural limits without breaking, and the deformed shape is retained after cooling.

For example, the annealing temperature of CuAlNi single crystal alloy is about 600° C. When heated to this temperature its shape may be drastically changed with very small applied forces. When cooled, the material retains the modified shape, and if it is rapidly cooled it also retains its shape memory qualities.

To shape-set a portion of elongated component of CuAlNi (or CuAlMn, CuAlBe, etc.), it is important that heating and cooling both be very rapid. Otherwise the material in the heat-affected zone adjacent to the heated portion may undergo precipitation, resulting in an altered composition, or it may form multiple crystals because of critical stress. Polycrystalline alloys have far less strain tolerance and recovery, so are much inferior in performance compared to single crystals.

If the objective is to make a bend in, for example, a wire, then it is necessary either to heat all of the wire uniformly or the heating and cooling must be done quickly.

Otherwise the wire in the heat-affected zone between the heated segment and the un-heated segment will be held at an intermediate temperature, above ambient but below the annealing temperature. In this intermediate temperature range, the single crystal (e.g., CuAlNi single crystal) is unstable and will degenerate rapidly to polycrystal form and be quite brittle.

Rapid cooling may be satisfactorily performed by submersion in salt water. Rapid heating is not as readily accomplished. Several methods are demonstrable: each has advantages and disadvantages.

Rapid heating can be accomplished by immersing the object to be shape-set in a very hot flame such as provided by an oxy-acetylene torch. The sample is held in the flame while it transforms and becomes straight, begins to glow, and then anneals. The sample is then quickly removed from the flame and, while constrained in the desired shape, it is plunged into salt water. Salt water is used because a layer of bubbles does not form to insulate the surface of the material.

Another method is to constrain the shape of the wire to the desired shape in a mold, heat the mold, and quench. Quench must be relatively fast, but in this case the specimen may be held at an elevated temperature (850-950° C.) for as long as is convenient.

For example, a CuAlNi wire is inserted in a stainless steel tube. The tube is heated to its annealing temperature (about 850° C.) and shaped by bending. Several bends may be incorporated. After bending, the tube is uniformly heated in an oven to 650-750° C. to anneal the CuAlNi, and then quickly quenched. The CuAlNi wire when removed from the stainless steel tube retains the modified shape: it has been shape-set.

A variation of this method is first to form a stainless steel tube into the shape desired, for example by heating segments in an acetylene flame and bending. After the tube is formed the CuAlNi wire is inserted into it at room temperature, and the tube with wire inside are heated and quenched. In this case it is important not to deform the CuAlNi too much as it may form multiple crystals. Re-crystallization occurs rapidly if CuAlNi is overstressed.

CuAlNi contained within a stainless steel tube is not ideal for rapid cooling. Cooling rate may be significantly enhanced by forming a number of holes in the tube to allow contact with the water and to reduce the insulating effect of air trapped within the tube.

Samples of hyperelastic CuAlNi heated to 950° C. in stainless steel tube and cooled by immersion in salt water have been found to be martensitic although shape-setting has taken place. The transition temperature may be reduced by re-heating the sample without the stainless steel mold and quenching it bare.

If deformation takes place prior to heating, strain must be limited to the plateau, about 9%, so as not to re-crystallize. If the sample is heated to near melting, then deformed and quenched, much larger deformations are tolerated.

In this example, stainless steel is used to constrain the deformed hyperelastic wire because the annealing temperature of stainless steel is higher than the temperature at which CuAlNi softens and becomes easily deformed. During heating, as the plateau stress of the hyperelastic material increases, the hyperelastic material exerts a great force. If a copper tube is used, its walls must be thick compared to the diameter of the hyperelastic. Otherwise, the force of the hyperelastic material shape recovery may cause the Cu tube to (partially) straighten because Cu anneals at a temperature lower than the softening temperature of hyperelastic material.

Another method is to heat the material by a laser beam or by an infrared heater. The beam may be moved onto the sample or vice versa. The technique works better if two beams are used, one on each surface. Quenching may be by spraying or dousing with salt water or other heat absorber.

Another method of rapid heating is by joule heating. A pulse of electrical energy is directed such that it is dissipated in the material, heating it to near incandescence. If heating is very rapid the material may be immersed during the heating phase, so that at the end of the joule heating pulse it immediately cools. Otherwise the sample may be moved so that it is immersed, or doused or sprayed with cold liquid.

The joule heating method is not limited to materials of small diameter. However, it is difficult to deliver the electrical energy into the SMA (e.g., CuAlNi, CuAlMn, CuAlBe, etc.) as they are typically very good electrical conductors (resistivity is of the order of 30 microhm-cm; pure copper is 1.5 microhm-cm.).

Still another method of heating is by induction heating.

These methods work best on material samples that are small in one dimension such as thin foils or fine wires.

Example of One Embodiment

A 1 mm diameter CuAlNi straight hyperelastic wire having a transition temperature at +10° C. was held in a curved shape with two pairs of pliers while being placed in an oxy-acetylene flame for approximately 3 seconds. The wire stiffened and straightened as it was heated, then softened and bent to a radius of about 5 mm. It was rapidly cooled by immersion in a pan of room-temperature salt water. After this procedure the wire retained a curvature of about 5 mm under no external stress, and returned to this shape after being straightened. This degree of curvature corresponds to a strain of approximately 10%, which compares favorably with the hyperelastic properties of the untreated wire, but with an altered shape.

Device Embodiments of the Invention

One application is as a flexure to replace hinges in eyeglasses. A strip of CuAlNi may be shape-set so that it is bent at a right angle. One end is attached to the frame; the other is attached to the temple piece of the glasses. A cam or eccentric may be included to provide two stable positions: with the glasses worn on the face, or with the glasses folded for transport or storage. Alternatively the entire glasses frame may be fabricated of CuAlNi single crystal wire by appropriate shape-setting.

Figure 1:
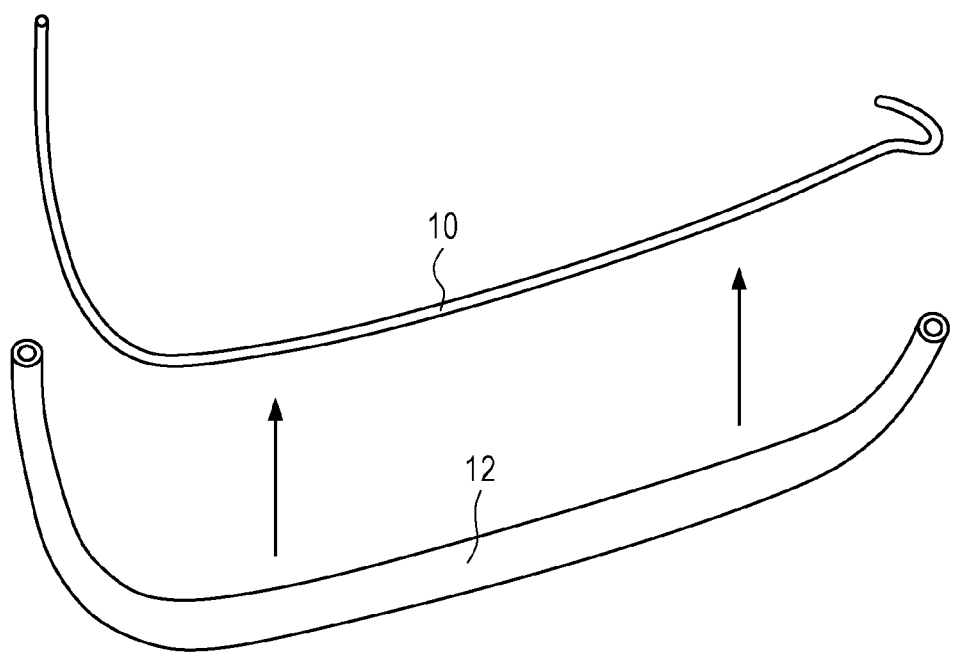
FIG. 1 is a side elevation view showing a hyperelastic wire superimposed over a steel mold used to form the wire.

As shown in FIG. 1, a hyperelastic wire 10 can be made in the desired shape by forming with the steps described above the wire within a tubular steel mold 12 which generally conforms to the wire shape.

EXAMPLE

Dental Arches

In this example, a dental archwire may be formed from a single-crystal SMA material (e.g., CuAlNi). The wire is heated by Joule heating, either as an electrical pulse or as a continuous electrical current, AC or DC, to annealing temperature. Typical currents are from 10 to 30 amperes. Voltage applied to the wire ends is typically 1 to 3 volts.

While it is at annealing temperature, the wire is quickly (less than 0.5 seconds) wrapped about a mandrel having the desired arch shape, and then plunged into a quenching bath. The sequence of heating, forcing the shape, and cooling may take less than a second.

In a first exemplary embodiment, an apparatus is used that consists of a variable voltage transformer, clamps or tubes that hold the wire ends in contact with the output (low-voltage) electrodes of the transformer, and a plunger with a U-shaped concavo-convex metal (copper) mandrel. This apparatus is illustrated in FIG. 4.

Figure 4:
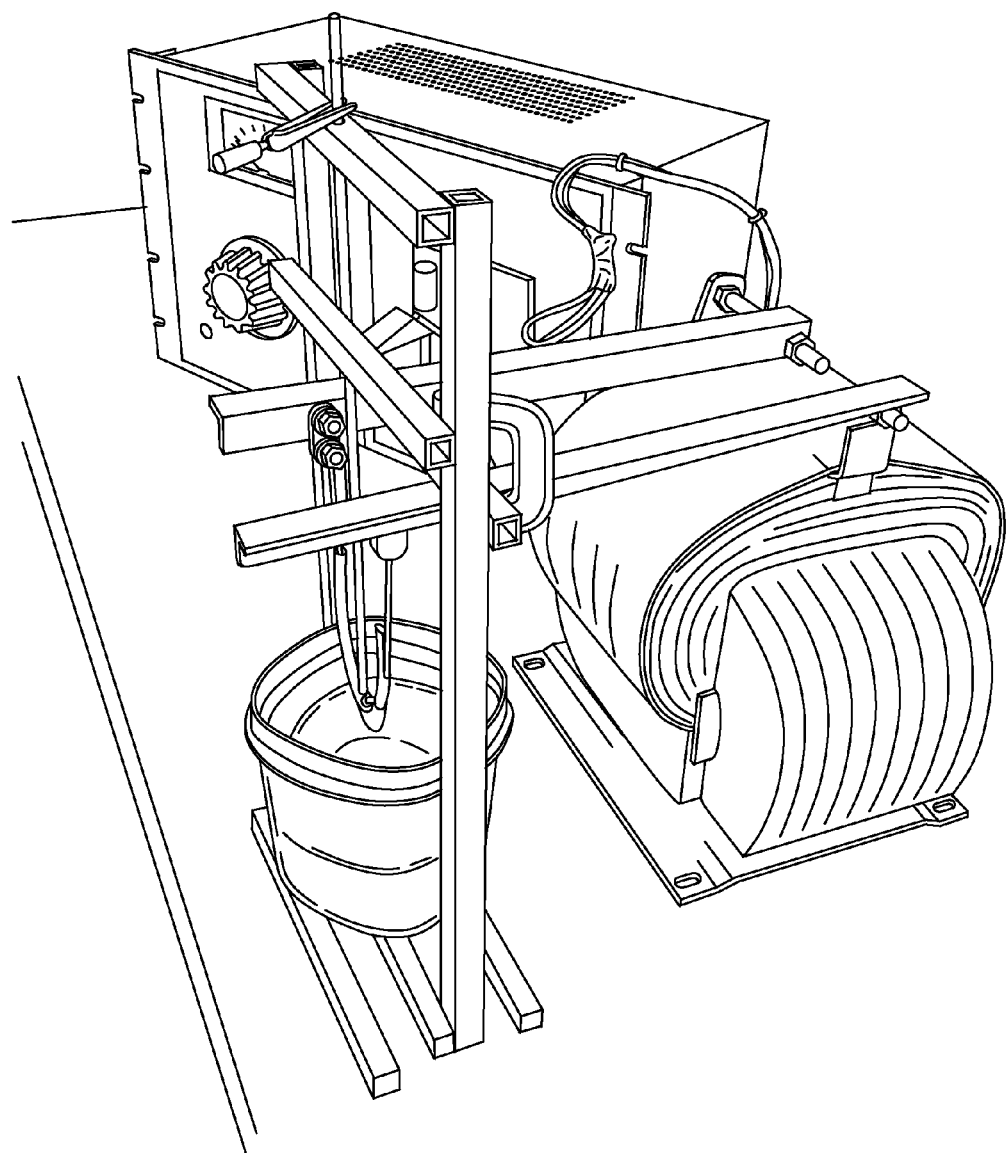
FIG. 4 illustrates one variation of an apparatus for shape-setting a hyperelastic material into an archwire.

In FIG. 4, the apparatus for shape-setting hyperelastic wires is shown and includes a Variac whose control knob is seen at the left side of the figure. The Variac supplies a stepped down voltage to the power transformer at center right in the figure. This transformer further steps down the AC voltage to a range of 1-3 volts, supplying a current of 10-40 amperes to the electrodes. These electrodes are two brass bars, suspended on a translucent plastic frame, extending from the power transformer electrical terminals to the hyperelastic wire. A portion of the hyperelastic wire may be seen below the forming mandrel, a U-shaped metal trough with flanges extending outward. The mandrel is prevented from falling onto the wire by a rod attached at the center of the U, extending through the translucent plastic frame and held temporarily by a clamp.

In operation, the process consists of heating the wire by current from the electrodes until it is annealed (greater than about 600° C.), then releasing (un-clamping) the forming mandrel with attached rod so that it falls onto the wire, forming the wire about the mandrel, disconnecting it from the electrodes, and forcing it into the vessel of quenching water. The heating process can be accomplished in less than 5 seconds: quenching takes place in a few milliseconds.

As mentioned, the mandrel may be suspended above the wire until the wire is heated to the desired temperature. Then the mandrel is released so that it falls by gravity against the heated wire. The force exerted on the wire by the mandrel as it falls pulls the wires from the clamps or tubes: this pulling force ensures that the wire is constrained to align with the inner groove shape of the mandrel. The mandrel immediately begins to absorb heat from the wire by contact, and then both the mandrel and the wire are quickly cooled by immersion in a water bath.

In this example, the mandrel is made of a single sheet of copper, thickness 0.005-0.020 inches, approximately 7 inches long and 0.5 inches wide. This sheet is folded along its long axis while being bent along the apex into a desired U shape with the edges pointed outward from the fold. This complex bend can be accomplished by lightly hammering the folded copper sheet into the desired U shape, with repeated annealing at a high enough temperature that the copper does not become work hardened. This technique is well known to metal art workers.

This method of shape-setting is applicable to any wire that it is desired to form into a simple curve, such as titanium-nickel based alloys that are commonly used for archwires.

In some variations, the wire forming the dental arch may have properties that vary along the length of the wire. For example, the dental arch may be formed and heat treated to give different regions or lengths of the dental arch different properties. For example, the properties of CuAlNi (and other shape memory alloys) enable another useful modification of dental arches as well as other applications. The additional properties may arise because different segments of the wire may be differently heat treated, thereby imparting different properties along its length. In dental arches this might be very useful: for example, the dental arch may be configured so that one part of the wire might pull on a tooth with a stronger force than another, or provide different rotation parameters for different teeth. Also, orthodontists are accustomed to making a sharp bend at the end of the wire to fix it in place. If the end of the wire is heated to annealing temperature and allowed to cool slowly, it will be in the martensite phase and hence will remain crooked rather than springing back after it is bent. This characteristic might be a desirable feature also for making it easier to load (or thread) the wire into the brackets that are attached to the teeth.

While particular forms of the invention have been illustrated and described herein, it will be apparent that various modifications and improvements can be made to the invention. Moreover, individual features of embodiments of the invention may be shown in some examples and not in others, but those skilled in the art will recognize that individual features of one embodiment of the invention can be combined with any or all the features of another embodiment. Accordingly, it is not intended that the invention be limited to the specific embodiments illustrated. It is intended that this invention to be defined by the scope of the appended claims as broadly as the prior art will permit.

What is claimed is:

1. A dental arch comprising a hyperelastic, single-crystal shape memory alloy, the dental arch having an elongate, shape-set curved length in an unstressed state that is configured to fit within a human mouth.

2. The dental arch of claim 1, formed by the method of:
heating a wire of single-crystal shape memory alloy to a first temperature sufficient for annealing the alloy;
forcing the wire into an arched shape while the wire is held at the first temperature, wherein the heating and forcing steps are performed in less than 10 seconds; and
rapidly cooling the alloy to room temperature sufficiently quickly to cause the alloy to remain a single-crystal in the arched shape.

3. The dental arch of claim 1, formed by the method of:

heating a wire of single-crystal alloy to an annealing temperature sufficient for annealing the alloy;

forcing the heated wire into a dental arch shape by forcing the wire against a mandrel, wherein the steps of heating and forcing the wire against the mandrel are performed in less than 10 seconds; and rapidly cooling the wire by quenching to a cooling temperature sufficiently quickly to cause the alloy to remain a single-crystal in the dental arch shape.

4. The dental arch of claim 1, wherein the curved elongate length has a round diameter of between about 0.013 to about 0.026 inches.

5. The dental arch of claim 1, wherein the curved elongate length has a rectangular cross-section with dimensions of between about 0.016 by 0.016 inches and about 0.020 by 0.030 inches.

6. The dental arch of claim 1, wherein the single-crystal shape memory alloy comprises a CuAlNi single crystal material.

7. The dental arch of claim 6, formed by the method of:

heating a wire of CuAlNi alloy to a first temperature sufficient to place the Cu, Al and Ni in solution;

rapidly quenching the alloy to a second temperature to prevent precipitation of the Cu, Al and Ni so that the alloy remains as a single-crystal of CuAlNi;

constraining the alloy into a dental arch shape;

heating the alloy to a third temperature for a first time period, wherein the third temperature and first time period are sufficient to cause the alloy to lose its strength; and cooling the alloy to a fourth temperature for a second time period, wherein the fourth temperature and second time period are sufficient to cause the alloy to remain a single-crystal in the shape.

8. The dental arch of claim 1, wherein the single-crystal shape memory alloy is selected from the group consisting of: CuAlMn single crystal material, CuAlBe single crystal material, and CuAlNb single crystal material.

9. The dental arch of claim 1, wherein the ends of the dental arch wire are in the martensitic phase at body temperature.

* * * * *

UNITED STATES PATENT AND TRADEMARK OFFICE
CERTIFICATE OF CORRECTION

PATENT NO. : 9,127,338 B2
APPLICATION NO. : 13/777216
DATED : September 8, 2015
INVENTOR(S) : Alfred David Johnson Page 1 of 1

It is certified that error appears in the above-identified patent and that said Letters Patent is hereby corrected as shown below:

In the Specification

In Col. 5, line 64, "10/588,412 filed Jul. 31, 2006," should read --10/588,413 filed Jul. 31, 2006,--.

Signed and Sealed this
Fifth Day of July, 2016

Michelle K. Lee
*Director of the United States Patent and Trademark Office*